United States Patent
Gramnas

[19]

[11] Patent Number: 6,159,248
[45] Date of Patent: Dec. 12, 2000

[54] KNEE PROSTHESIS

[75] Inventor: Finn Gramnas, Kinna, Sweden

[73] Assignee: Gramtec Innovation AB, Kinna, Sweden

[21] Appl. No.: 09/250,577

[22] Filed: Feb. 16, 1999

Related U.S. Application Data

[60] Provisional application No. 60/083,318, Apr. 28, 1998.

[30] Foreign Application Priority Data

Jul. 13, 1998 [SE] Sweden .................................. 9802515

[51] Int. Cl.[7] ...................................................... A61F 2/64
[52] U.S. Cl. .............................................................. 623/44
[58] Field of Search .......................................... 623/41–45

[56] References Cited

U.S. PATENT DOCUMENTS

| | | | |
|---|---|---|---|
| 2,551,537 | 5/1951 | Havens | 623/44 |
| 3,694,823 | 10/1972 | May | 623/44 |
| 3,723,997 | 4/1973 | Kolman | 623/44 |
| 3,934,273 | 1/1976 | Mortensen | 623/44 |
| 3,982,279 | 9/1976 | Valenti et al. | 623/44 |
| 4,206,519 | 6/1980 | Blatchford et al. | 3/27 |
| 4,351,070 | 9/1982 | Blatchford | 3/27 |
| 5,755,813 | 5/1998 | Krukenberg | 623/44 |
| 5,899,943 | 5/1999 | Shiraishi et al. | 623/44 |

FOREIGN PATENT DOCUMENTS

| | | | |
|---|---|---|---|
| 2023040 | 5/1970 | Germany | 623/44 |
| 2161386 | 1/1986 | United Kingdom | 623/44 |
| WO 97/10781 | 3/1997 | WIPO | A61F 2/64 |

*Primary Examiner*—Bruce Snow
*Attorney, Agent, or Firm*—Gardner, Carton & Douglas

[57] ABSTRACT

A knee prosthesis has two pivotally interconnected members (10,11) carrying a locking device (17) and a first end a second axle (20,21). The first axle (20) forms a bearing axle for the locking device and the second axle (21) cooperates with the locking device for activation thereof. The second axle (21) is located at a distance behind the first axle (20) and is arranged to act upon the locking device in such a way that when the line of action (26) from a load on the knee prosthesis passes through the second axle (21) or between the first (20) and the second axle, said second axle will act upon the locking device to activate it, while when said line of action (26) passes through the first axle or in front of it the second axle (21) will be unloaded and the locking device (17) inactivated.

5 Claims, 15 Drawing Sheets

KNEE PROSTHESIS

This application claim benefit to application 60/083,318 filing date Apr. 28, 1998.

TECHNICAL FIELD

The present invention refers to a knee prosthesis comprising two pivotally interconnected members carrying a locking device and a first and a second axle, said first axle forming a bearing axle for the locking device and the second axle cooperates with the locking device for activation thereof, said locking device is arranged to permit said members to pivot in an unloaded position but prevent pivoting from extended to bent position when loaded.

BACKGROUND OF THE INVENTION

Traditional friction locks in knee prosthesis will lock when there is a load acting on them, i e when some part of the body weight rests on the artificial knee. This takes place in a still standing position as well as during the walking phase at heel strike when the heel hits the ground, and during toe off supporting oneself on the toe while extending the leg to initiate the swing phase when the leg swings freely in the air.

At normal walking without a prosthesis one starts already during toe off to flex the knee-joint to initiate the swing phase before all body weight is has been removed from the leg in question. This is not possible with knee prosthesis with a friction lock of the conventional kind. This involves an unnatural walking and makes walking in stairs and broken ground and cycling difficult since the knee prosthesis will lock as soon as it is loaded.

Knee prosthesis with friction locks in the form of a brake drum are disclosed in U.S. Pat. No. 4,206,519 and 4,351, 070. In the last mentioned document there is a linkage transferring motions in the hip axis to the locking device in order to control the locking function thereof in response to the torque of the hip axis.

WO 97/10781 discloses a knee prosthesis with a friction lock in the form of a resiliently deformable substantially C-shaped member cooperating with an axle. The C-shaped member can be rotated about the axle in unloaded position, but in a locked position be deformed and locked to the axle. The subject and most important features of the invention It is an object of the invention to provide a knee prosthesis of the kind mentioned above, which permits rotation of the knee-joint in unloaded position and when it still is under body load during toe off when supporting oneself on the toe while extending the leg to initiate the swing phase, but which locks against rotation from extended to flexed position at other loaded positions, i e during heel strike when supporting oneself on the heel and during mid stance when supporting oneself on the whole foot. This has according to the invention been achieved by the fact that the second axle is located at a distance behind the first axle and is arranged to act upon the locking device in such a way that when the line of action from a load on the knee prosthesis passes through the second axle or between the first and the second axle, said second axle will act upon the locking device to activate it, while when said line of action passes through the first axle or in front of it the second axle will be unloaded and the locking device inactivated.

A further important advantage of the invention is that the knee-joint has a freewheel effect in such a way that it can always rotate from flexed to extended position also under load. By this for example walking in stairs will be possible.

The knee-joint will however lock immediately again if it is rotated in the opposite direction, i e from extended to flexed position, under such load that the locking device is activated.

DESCRIPTION OF DRAWINGS

The invention will below be described more in detail with reference to some embodiments shown in the accompanying drawings.

DESCRIPTION OF EMBODIMENTS

The knee prosthesis according to the embodiment shown in FIGS. 1–4 comprises an upper and a lower member 10 and 11 which are pivotally interconnected. The upper member is intended to be attached to a prosthesis sleeve 12 and the lower member to a lower leg prosthesis 13 (FIG. 4) having a foot prosthesis 13a connected thereto.

Figure 1:
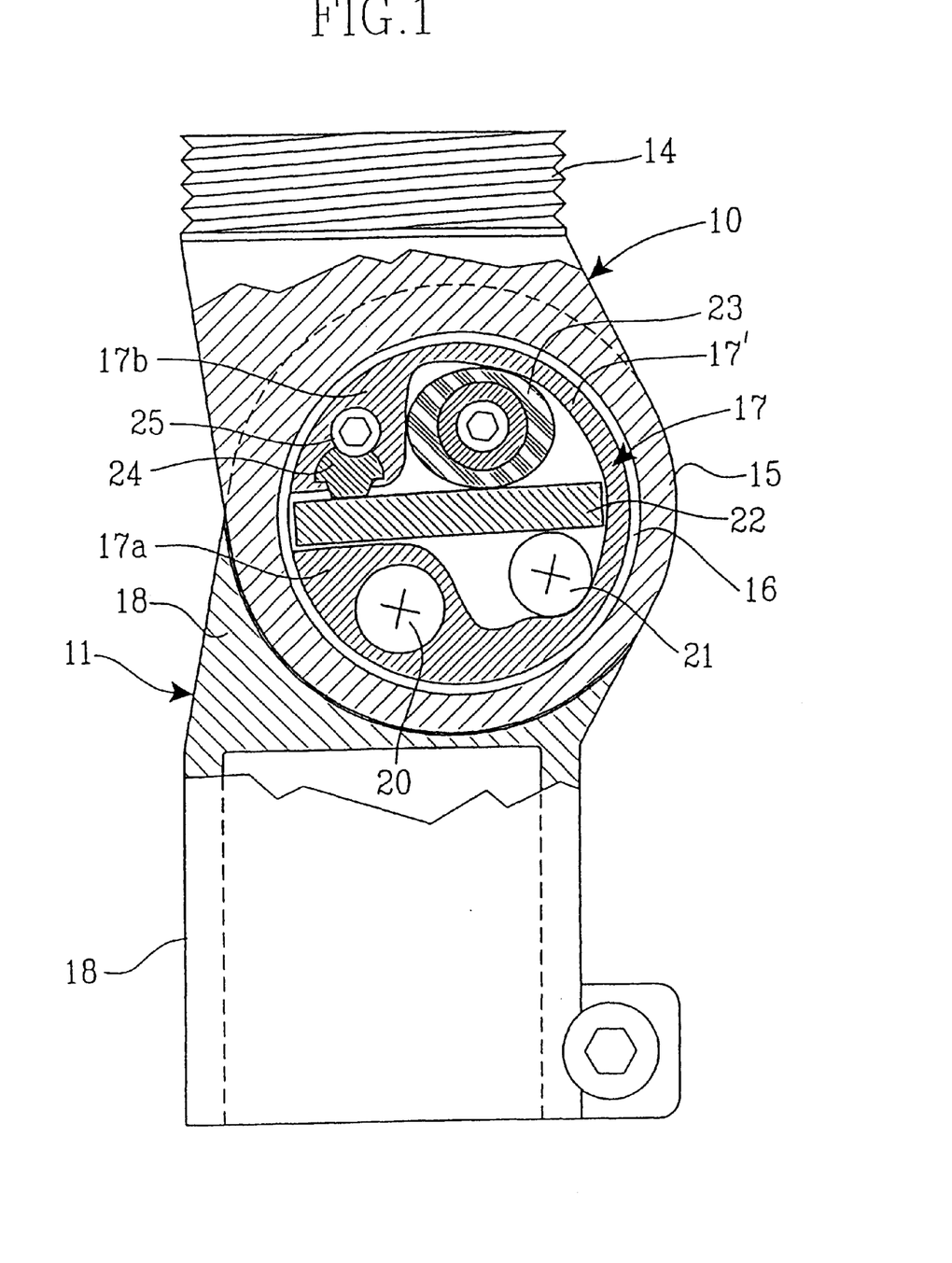
FIG. 1 is a longitudinal section through an embodiment of a knee prosthesis according to the invention in unloaded position.
Figure 2:
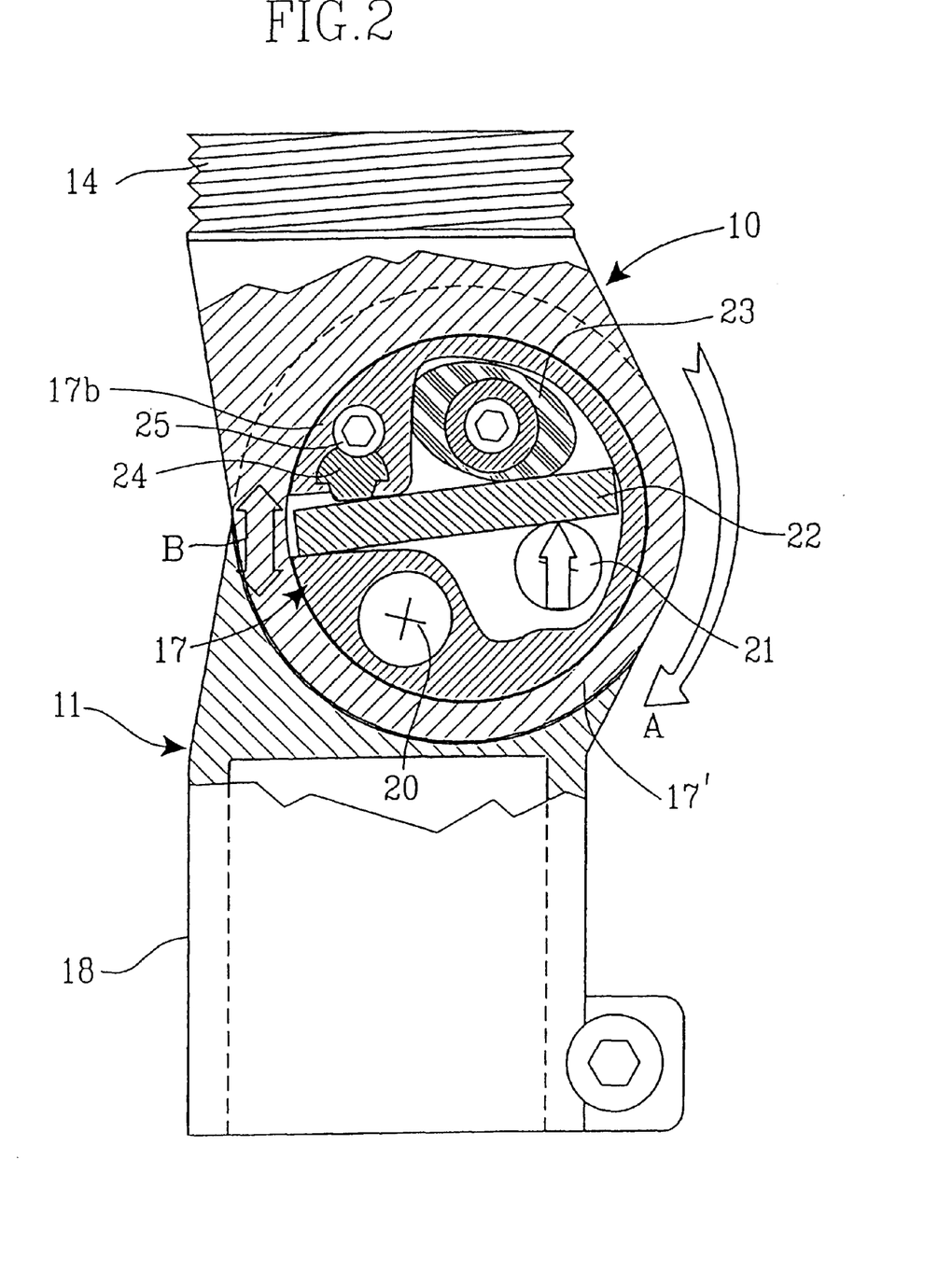
FIG. 2 shows the knee prosthesis according to FIG. I in loaded position.
Figure 3:
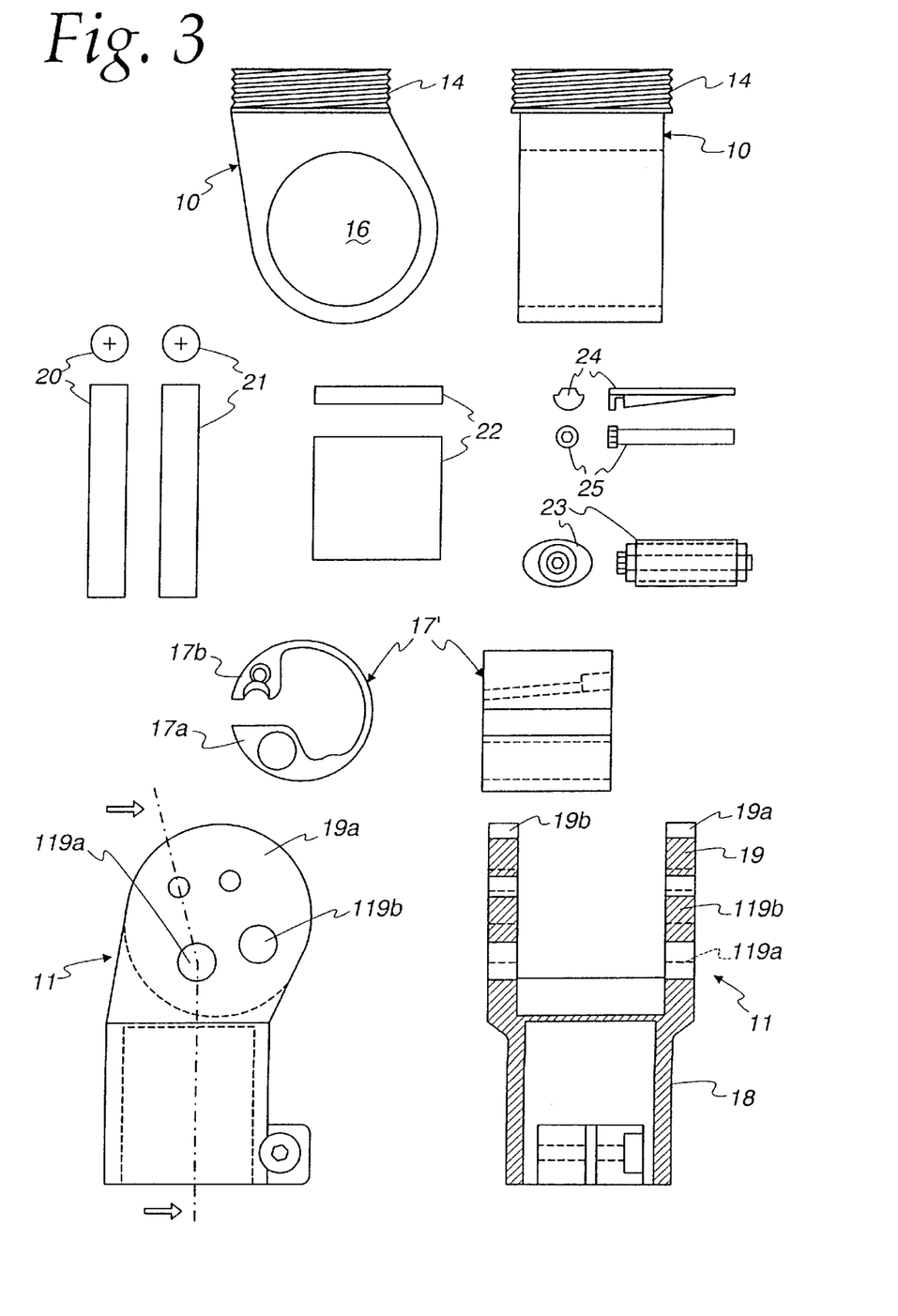
FIG. 3 is an exploded view of the knee prosthesis according to FIGS. 1 and 2.

The upper knee prosthesis member 10 comprises a socket, in the shown embodiment a threaded socket 14, for connection to a prosthesis sleeve, and a housing portion 15 with a through opening 16 for receiving a locking device in the form of a brake drum 17'. The lower knee prosthesis member 11 is provided with a sleeve-shaped socket 18 for connection to a lower leg prosthesis 13, and a yoke-shaped upper portion 19 between the shanks 19a and b of which the housing portion 15 of the upper knee prosthesis member 10 is received.

Two axles 20 and 21 extend substantially in parallel through holes 119a and 119b, respectfully formed in the shanks 19a and 19b and through and the brake drum 17' arranged in the housing portion 15. The brake drum 17' is pivotally mounted about the first axle 20. The second axle 21 passes right through the open space in the brake drum 17' and forms a part of the activation mechanism for the braking function of the knee prosthesis in a way which will be described more in detail below. The second axle 21 is arranged at a certain distance behind the first axle 20.

In the braking mechanism there is included besides the brake drum 17' an activating member 22 in the form of a lever arm extending through the brake drum 17' substantially across the axles 20 and 21. The brake drum 17' has the shape of an open ring and the lever arm 22 extends in between the shanks 17a and b of the brake drum. The lever arm 22 supports against the second axle 21 and can thereby be pressed upwards and in such a way force the shanks 17a and b to spring apart, at which the brake drum 17' expands and is friction locked against the inside of the opening 16. Between the lever arm 22 and the brake drum 17' on the opposite side of the lever arm with respect to the second axle 21 there is arranged an adjustable resilient element 23 against which the lever arm presses when it is activated by the second axle 21, said resilient element 23 thus limiting the action of the lever arm 22. The resilient element 23, which comprises a sleeve through which a screw 23a extends, can be made stiffer in order to adapt to the bodyweight of the wearer of the prosthesis and thus prevent that the knee-joint will lock too easily. The stiffness of the element 23 can be adjusted either by tightening the screw 23a at which the sleeve is compressed, or by replacing the element 23 for stiffer or softer rubber element 23.

The lever arm 22 can possibly be made resilient to some extent, e g be made of a number of spring steel elements placed on top of each other, at which it will be possible to accomplish the light resilient knee flexion one normally makes when putting the heel in the ground, so called stans flex. The element 23 must in this case be relatively soft.

One shank 17a of the brake drum 17' holds a bearing for the first axle 20 while the second shank 17b supports friction adjustment means 24,25 for controlling the friction level during the different phases of the walking cycle. These friction adjustment means comprises a conical wedge 25 and a screw 24 cooperating therewith. By tightening the screw 24 the wedge 25 is moved and can expand the brake drum 17'. A friction adjustment could alternatively be done by squeezing together the shanks 19a and b of the yoke-shaped part 19. A brake lining, e g a plastic band, could be arranged on the outside of the brake drum.

In FIG. 1 the knee-joint is shown in a position where the brake drum 17' is unloaded and thus can be rotated within the opening 16 of the housing portion 15. If however a load (FIG. 2) is applied on the leg the brake drum 17' will be pressed downwards and at the same time rotate about the first axle 20 in the direction of the arrow A. When the brake drum is rotated about the axle 20 the rear brake-activation axle 21 will meet the lever arm 22, which as described above forces the brake drum 17' to expand (arrow B) and lock against the inside of the opening 16 in the housing portion 15. The knee joint is by this locked.

If the knee joint is rotated from flexed to extended position, i e in the opposite direction with respect to the arrow A, during loading, the friction between the inside of the opening 16 in the housing portion 15 and the brake drum 17' will force this to rotate back to the position form unloaded position (dashed lines). The lever arm 22 will then leave the axle 21 and the knee joint can be rotated freely in counter clockwise direction. It will however immediately lock again if it during loading will be rotated in clockwise direction.

Figure 4A:
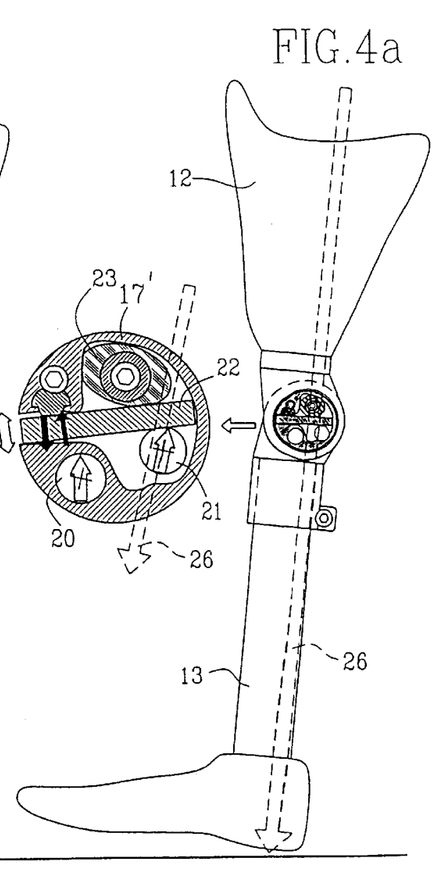
FIGS. 4a–f illustrates the function of the knee prosthesis during the different phases of the walking cycle.

In FIGS. 4a–f the braking function of the knee prosthesis is shown during the different phases of the walking cycle. In FIG. 4a the heel strike position is shown, in which the heel strikes the ground and the wearer starts to put load on the leg in question. The body weight line illustrated by the arrow 26 in this position passes right through the second axle 21 or behind this, which means that the whole body weight will force the brake drum 17' to rotate downwards about the axle 20. The lever arm 22 will then meet the axle 21, which in turn presses against the lever arm 22 which forces the brake drum 17' to expand and lock the knee joint prosthesis. If the bending force would increase the knee joint will use the front axle 20 as a fixed point and the distance between the axles 20 and 21 will act as a lever arm and increase the braking force proportionally to the increasing bending force. This will keep the knee locked independently of the bending forces which act upon the knee joint.

Figure 4B:
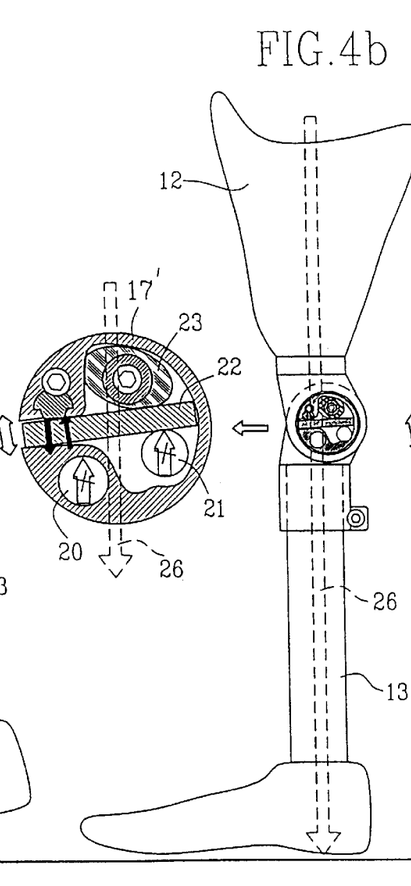

In FIG. 4b is shown the mid stance position when the whole foot rests against the ground and the body weight acts essentially right through the leg in parallel therewith. The body weight line 26 passes in this position between the two axles 20 and 21, which means that both the front 20 and the rear axle 21 are loaded, at which the latter still presses against the lever arm 22 and locks the brake drum 17'. If the prosthesis wearer in this position would try to flex the knee joint this would only lead to an increased force on the rear brake-activating axle 21 in the way described above.

Figure 4C:
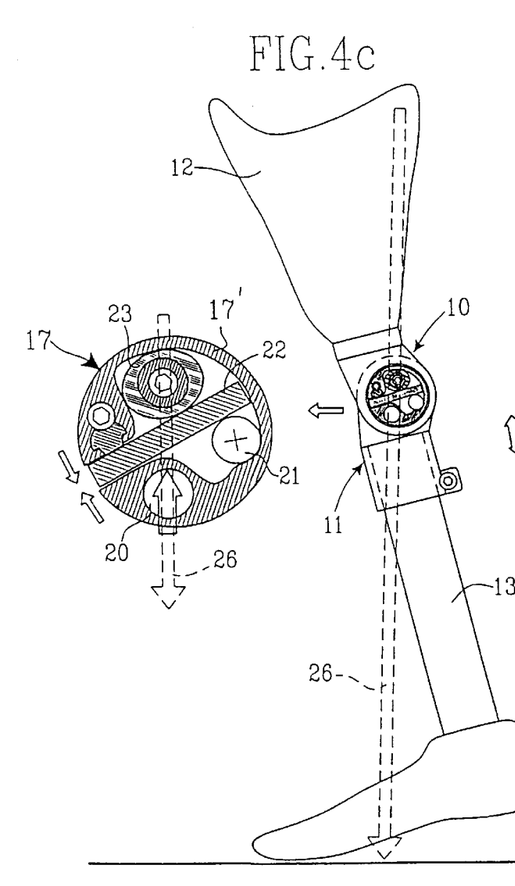

In FIG. 4c is shown the toe off phase when supporting oneself on the toe while extending the leg to initiate the swing phase with the leg swinging freely in the air. A part of the body weight rests in this position still upon the leg. At normal walking a flexing of the knee joint takes is initiated already in this position in order to initiate the swing phase before all body weight has been removed from the leg in question. The body weight line 26 passes in this position from the toe part of the foot prosthesis 13a through or in front of the front axle 20, the bearing axle, at which the body weight rests on the front axle 20. No load acts on the rear brake-activation axle 21, at which the knee joint is free to rotate for initiating the swing phase of the walking cycle.

Figures 4D, 4E, 4F:
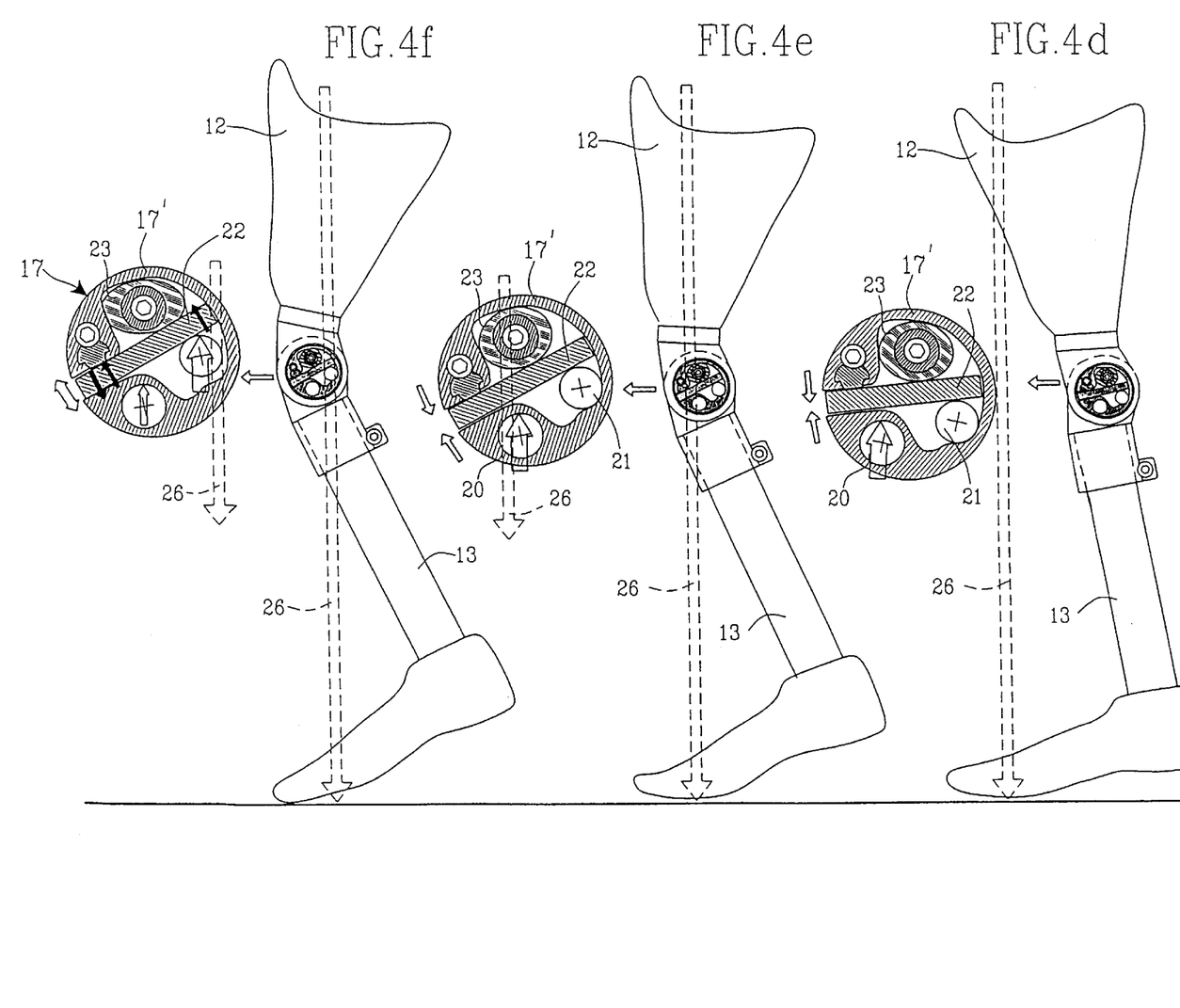

In FIGS. 4d–f are shown different stages of the initiation of the swing phase of the walking cycle with the knee joint prosthesis in different positions. In FIG. 4d is shown an extended leg in toe off position at which the body weight line 26 passes from the toe portion of the foot prosthesis 13a and in front of the front axle 21. In a corresponding way as described in connection with FIG. 4c the brake function is inactivated despite that body weight is still loading the leg and the knee joint can be flexed for initiating the swing phase.

FIG. 4e shows the toe off position with the knee flexed approximately 45°. Most of the body weight has now been removed from the leg, but there can still be enough load for activating the brake function. However the body weight line 26 will still be in front of the front axle 20, and no load will act upon the rear brake-activation axle 21. If however the prosthesis wearer in this position would stumble the body weight can be moved backwards by extending the thighbone and by that have the brake activated.

In FIG. 4f is shown the end of the toe off phase just as the leg has been unloaded from the body weight. The leg is now flexed approximately 55° and the body weight line 26 passes through the rear brake-activating 21, but since the leg is unloaded the knee joint can be rotated. If however the prosthesis wearer in this position would stumble or something else unexpected would happen the prosthesis wearer can activate the brake by extending the thighbone.

Figure 5A:
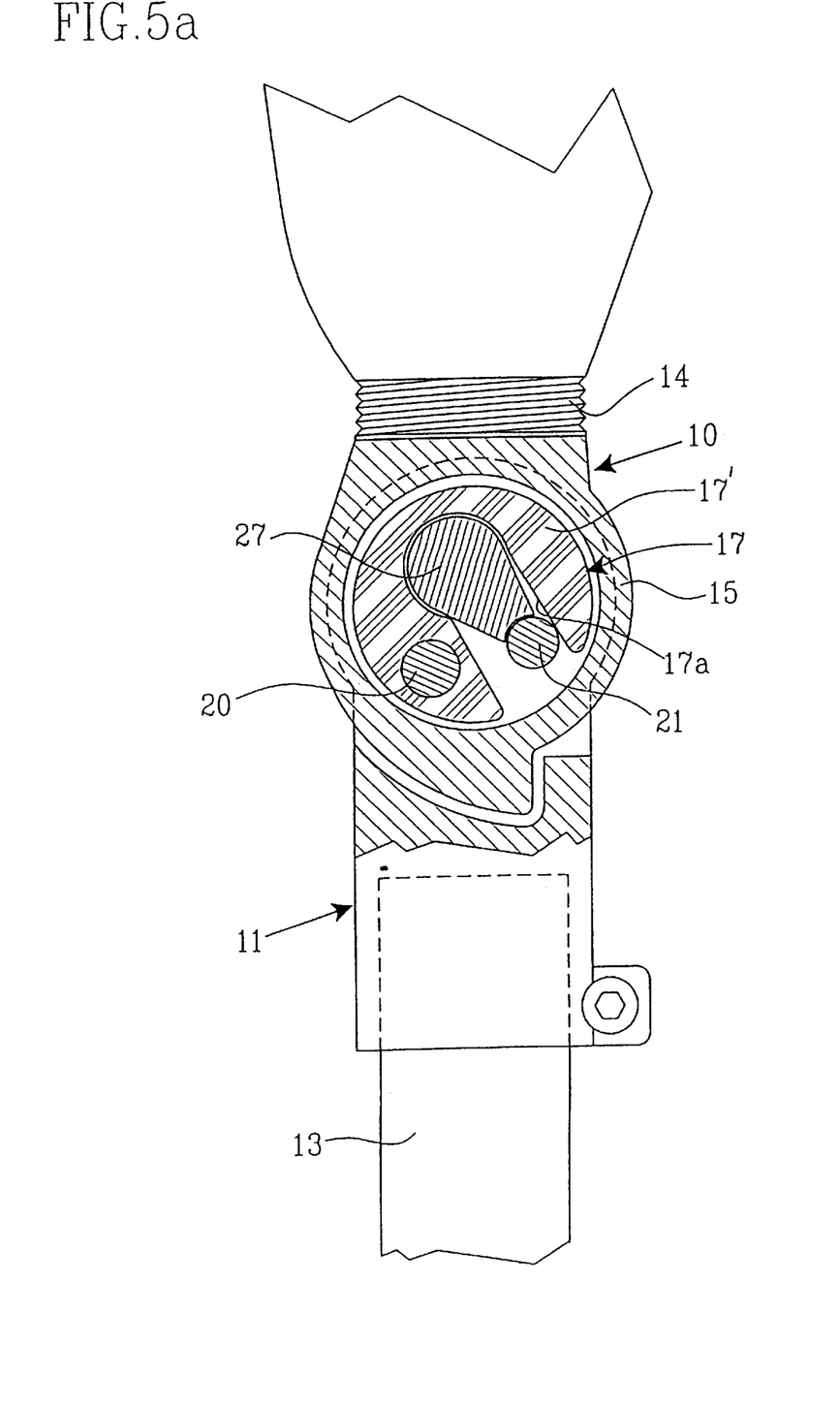
FIGS. 5a and b show longitudinal sections through a second embodiment of the knee prosthesis in unloaded and loaded positions respectively.
Figure 5B:
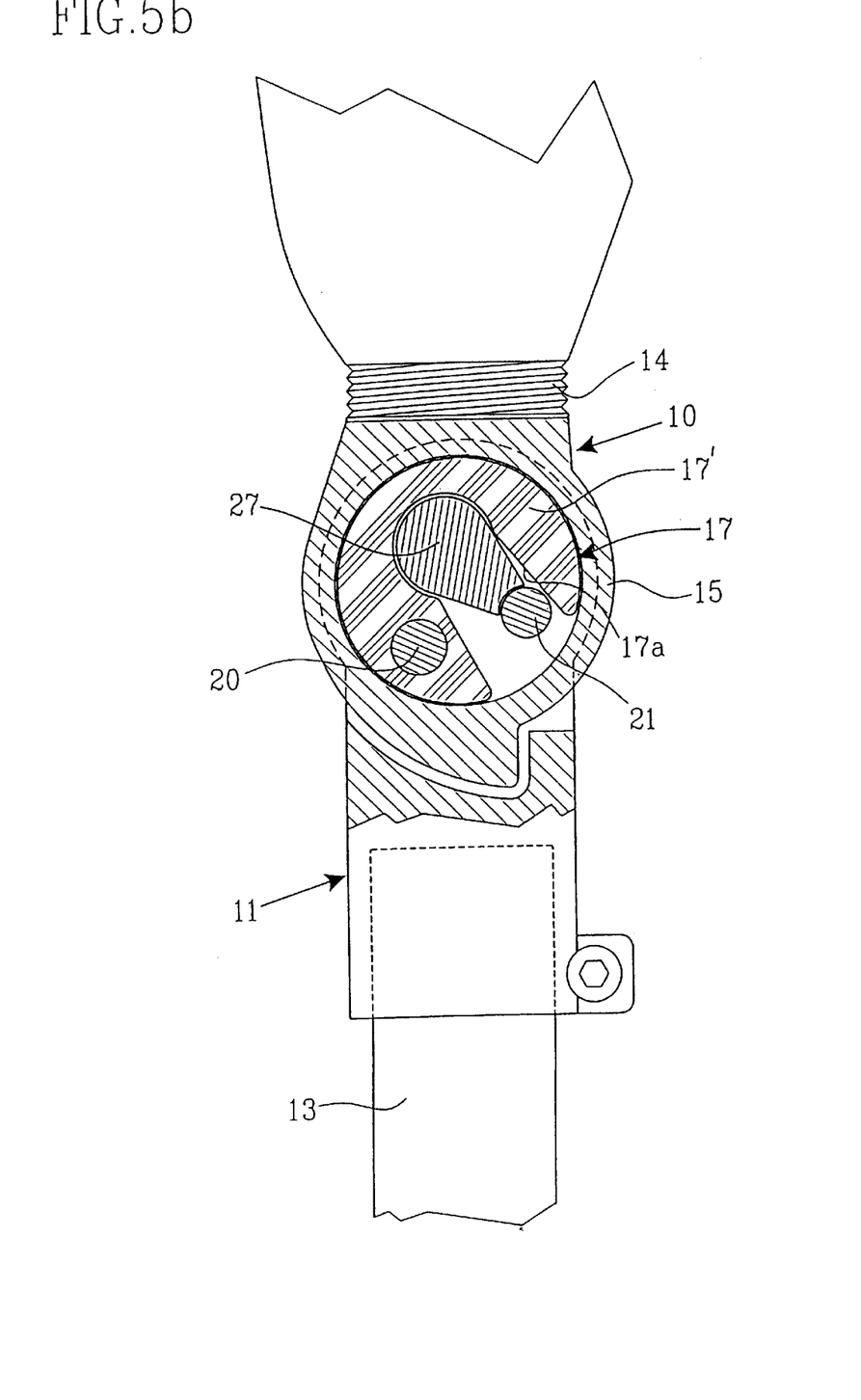

The embodiment shown in FIGS. 5a and b differs from the one described above by the fact that the brake-activating axle 21 acts directly upon an inclined end surface 27 on the shank 17b of the brake drum 17'. This embodiment functions in a corresponding way as the previous one since the brake drum 17' in unloaded position (FIG. 5a) can be rotated in the opening of the housing portion 15. In such loaded positions (FIG. 5b) when the body weight line passes between the axles 20 and 21 right through the second axle 21 or behind it, the body weight will force the brake drum 17' to rotate downwards about the axle 20. The inclined surface 27 on the brake drum will then meet the axle 21, which forces the brake drum 17' to expand and lock against the inside of the housing portion 15, at which the knee joint is locked. In the positions when the body weight line passes through or in front of the front axle 21, i e the bearing axle, and no load acts upon the rear brake-activating 21, the knee joint will be free to flex.

Figure 6A:
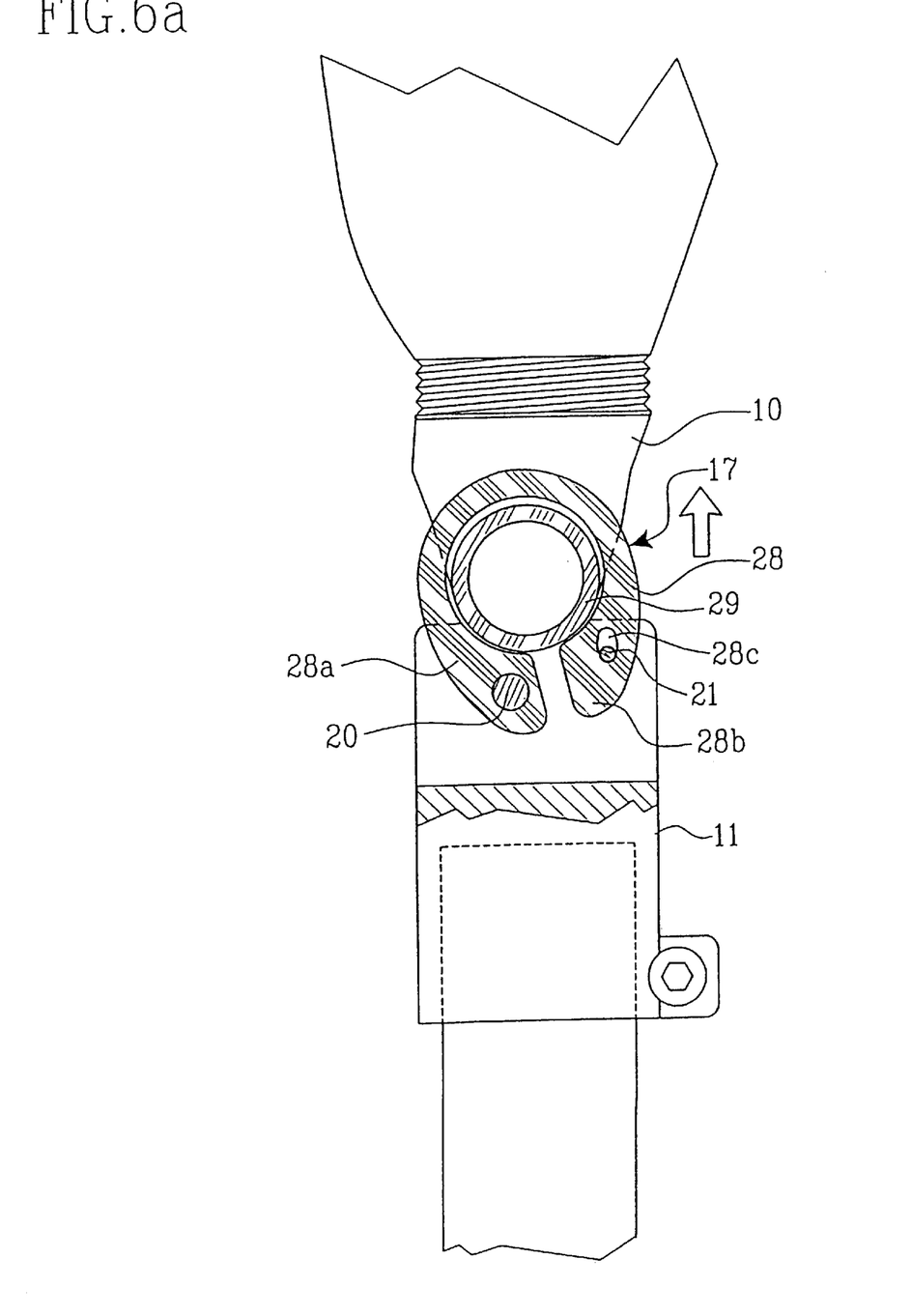
FIGS. 6a and b show longitudinal sections through a third embodiment of the knee prosthesis in unloaded and loaded positions respectively.
Figure 6B:
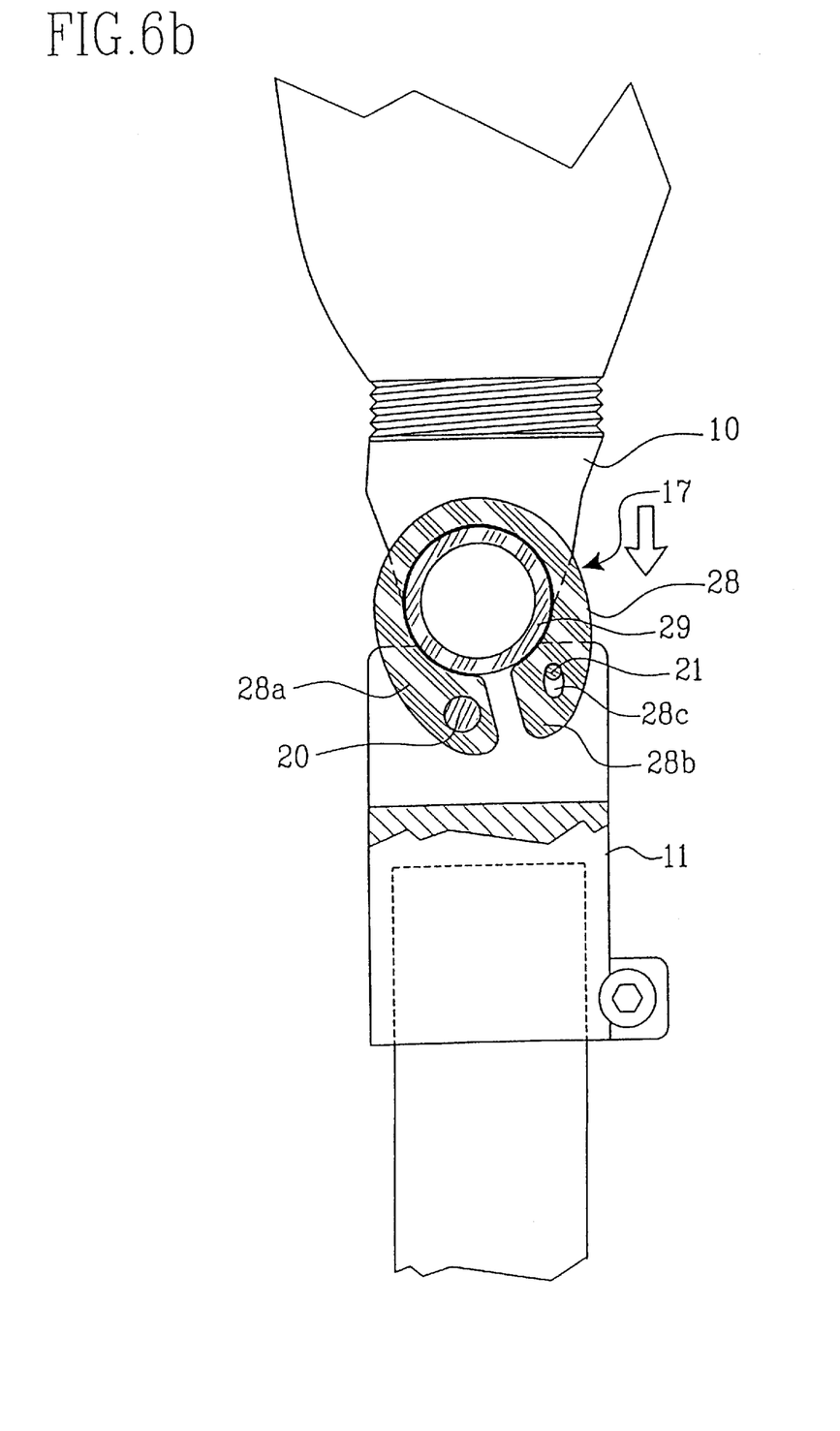

In FIGS. 6a and b it is shown an embodiment where the knee joint has a friction lock in the form of a substantially C-shaped resilient member 28 arranged about a tube-shaped axle 29 connected to the upper prosthesis member 10. The first axle 20 extends through one shank 28a of the C-shaped member 28 and the second brake-activating axle 21 extends through the second shank 28b of the C-shaped member 28 through a groove 28c arranged therein.

In unloaded position (FIG. 6a) and in a position where the line of action from a loading on the knee prosthesis passes through the first axle 20 or in front thereof the C-shaped member 28 will be unloaded and rotatable about the axle 20 and slidable on the inner tube-shaped axle 29. If however the knee joint is loaded (FIG. 6b) in such a way that the line of action passes through the second brake-activating axle 21 or between the first and the second axle 20, 21 the body weight will force the member 28 to rotate downwards about the axle 20. The shank 28b of the C-shaped member 28 can only be moved in the direction permitted by the groove 28c, which extends in such a direction that the shank 28a when the knee joint is loaded will clamp about the inner tube shaped axle 29, at which the knee joint is locked.

Figure 7A:
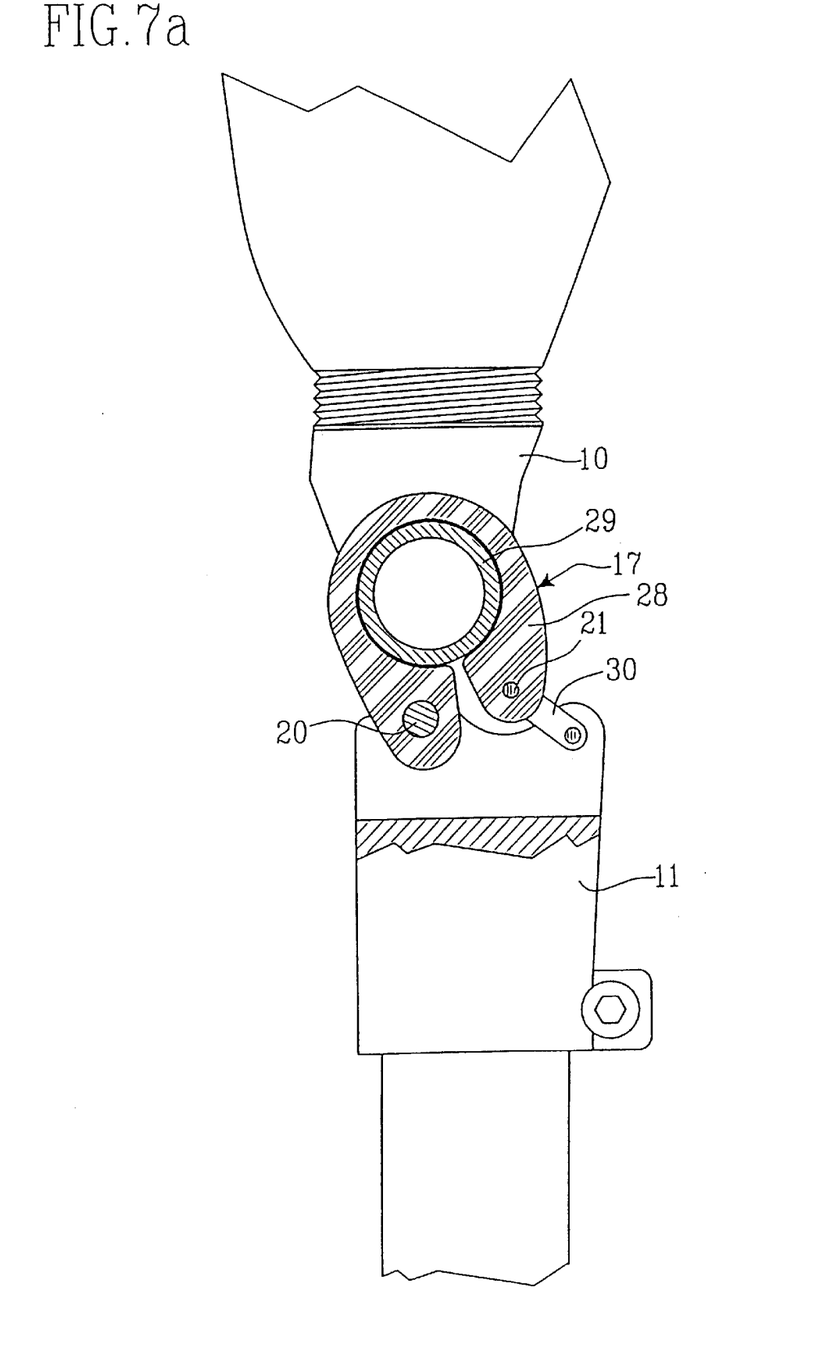
FIGS. 7 shows longitudinal sections through a fourth embodiment of the knee prosthesis in unloaded and loaded positions respectively.
Figure 7B:
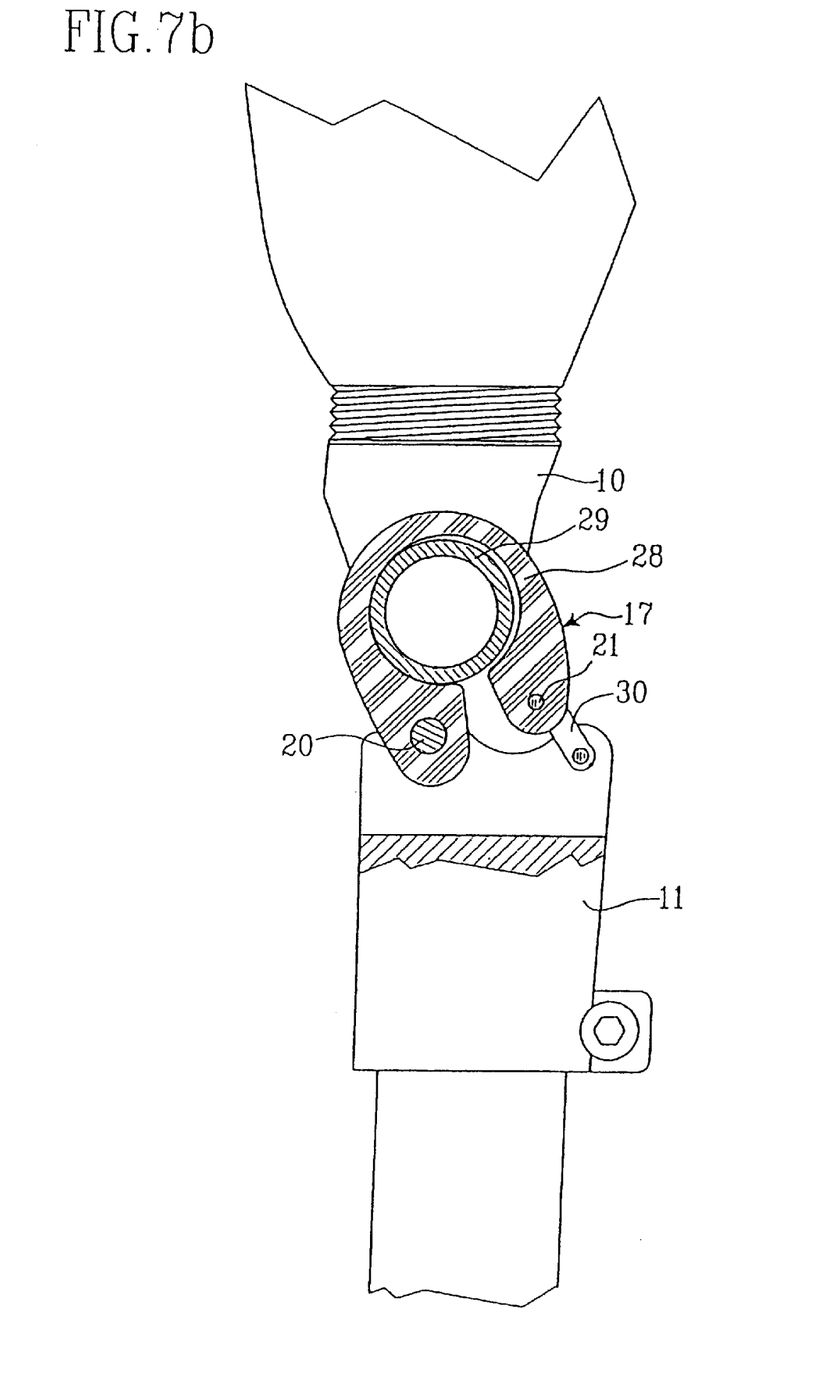

In FIG. 7 it is shown a further embodiment, which differs from the one shown in FIG. 6 by the fact that the brake-activating axle 21 is connected with the lower prosthesis member 11 by means of a link 30. In an unloaded position at which the C-shaped member 28 is free to rotate about the axle 21 and slide on the inner tube-shaped axle 29. If however the knee joint is loaded in such a way that the line of action passes through the second brake-activating axle 21 or between the first and the second axle 20, 21 the body weight will force the member 28 to rotate downwards about the axle 20. The link 30 will then force the shank 28a to clamp about the inner tube-shaped axle 29, at which the knee joint is locked, as is shown in FIG. 7.

Figure 8:
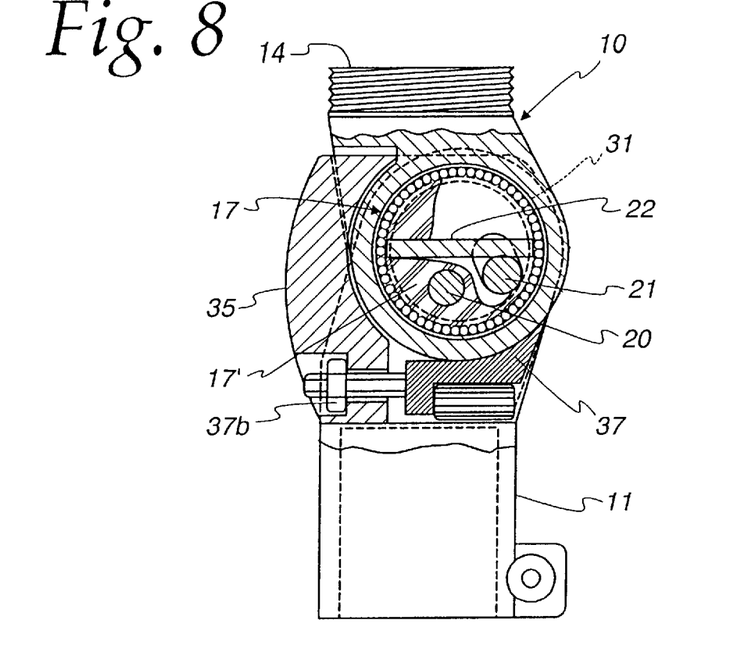
FIG. 8 shows a longitudinal section through a fifth embodiment of the knee prosthesis in unloaded position.
Figure 9:
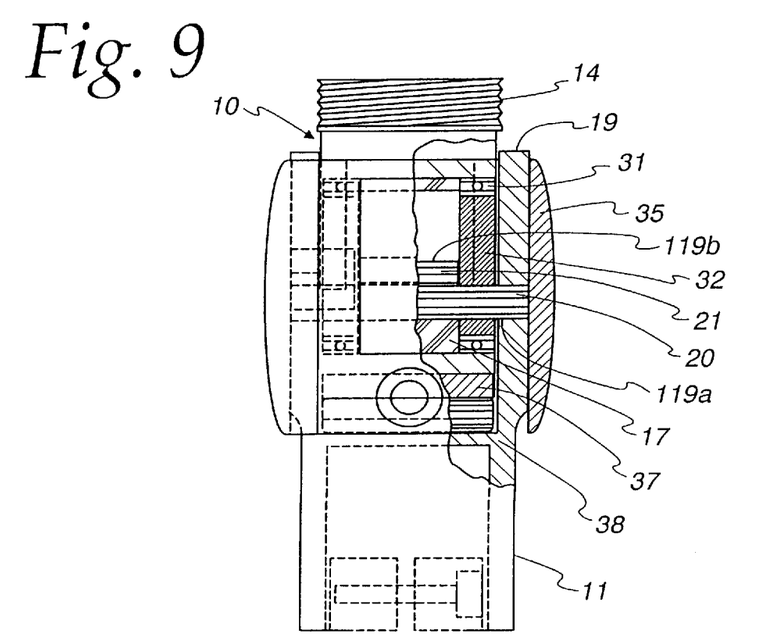
FIG. 9 is a front view of the knee prosthesis according to FIG. 8.
Figure 10:
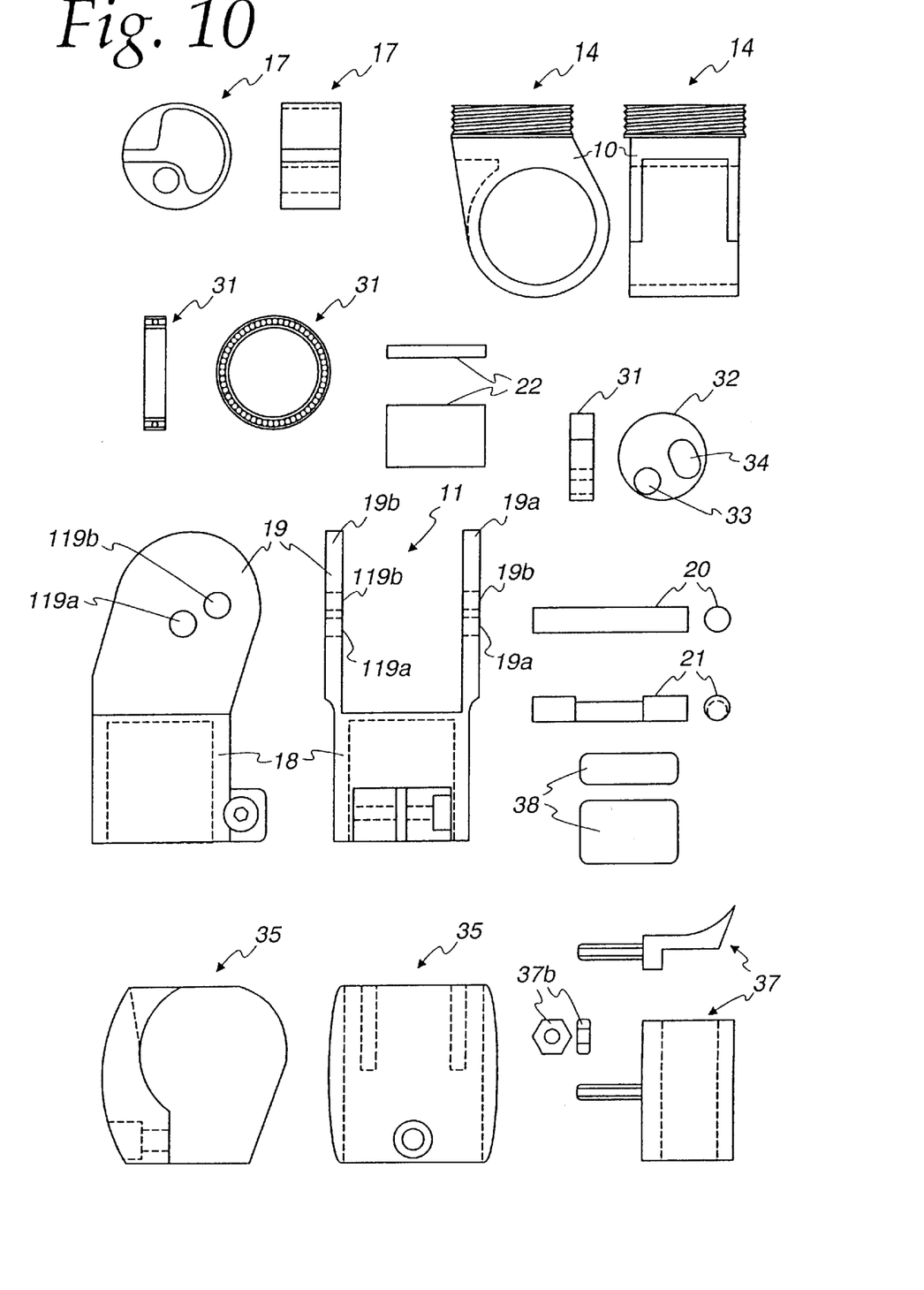
FIG. 10 is an exploded view of the knee prosthesis according to FIGS. 8 and 9.

The embodiment according to FIGS. 8–10 is similar to the one shown in FIGS. 1–4 and differs mainly therefrom by the fact that the brake drum 17' has been made shorter in order to make space for a ball bearing 31 on both sides. By this the lateral stability of the knee joint is improved. The stabilization of the ball bearings 31 is transferred via a plate 32 placed in the center of the bearings, said plate having a hole 33 for the front axle 20 and an oblong hole 34 for permitting the brake-activating movement of the second axle 21. The resilient element 23 in the embodiment according to FIGS. 1–4 has been replaced by a functionally corresponding member 38. The friction adjusting means 24–25 according to FIGS. 1–4 has been replaced by the parts 35, 37 and 39.

The upper knee joint member 10 has a lower part-cylindrical outer surface 10a. The housing member 35 is attached to the lower knee joint member 11 by means of the adjusting means 37 and the nut 37b. The resilient element 38 is placed under the adjusting means 37 and will assist this to press the upper knee joint member 10 and its part-cylindrical surface 10a against the housing portion 35 and its corresponding surface 35a. If the nut 37b is tightened the adjusting means 37 will press harder against the resilient element 38 since this is forced to slide downwards along the part-cylindrical surface 10a. The upper knee joint member 10 will then be clamped between the adjusting means 37 and the housing portion 35 actuated by the compressed resilient element 38. This gives a frictional resistance as the knee joint member 10 is rotated. The inner brake drum is now not needed for braking the swing movement of the leg but only be used for locking the knee joint. The resilient element 38 has also the same function as the element 23 in FIG. 3. In order to load the brake drum 17' and the upper knee joint member 10 until a rotation is initiated about the first axle 20 and activate the brake, the resilient element 38 has to be compressed via the adjusting means 37 in the movement about the first axle 20.

Figure 11:
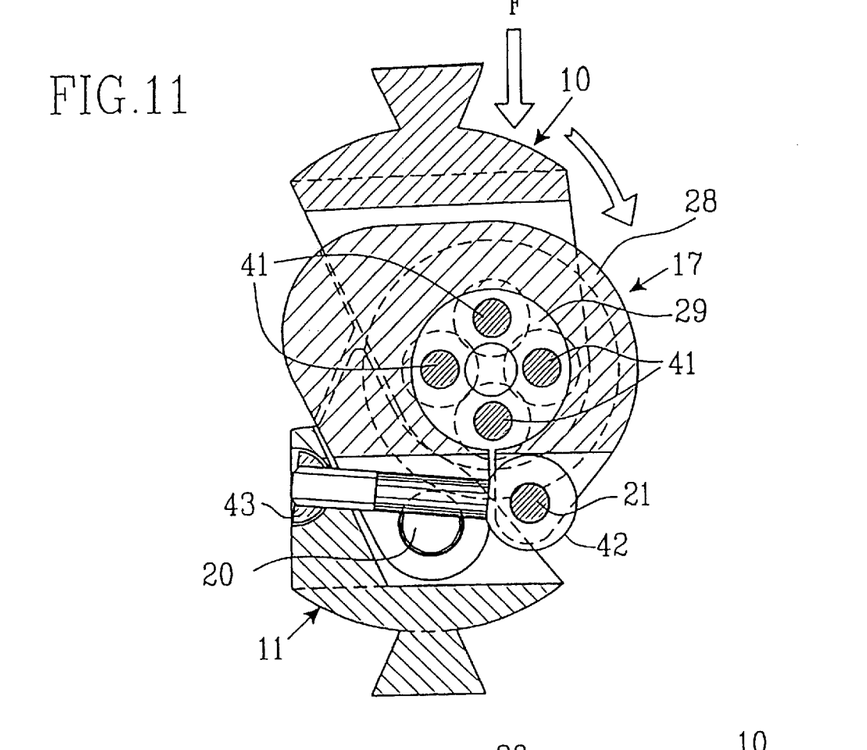
FIG. 11 is a longitudinal section through a sixthe embodiment of the knee prosthesis.
Figure 12:
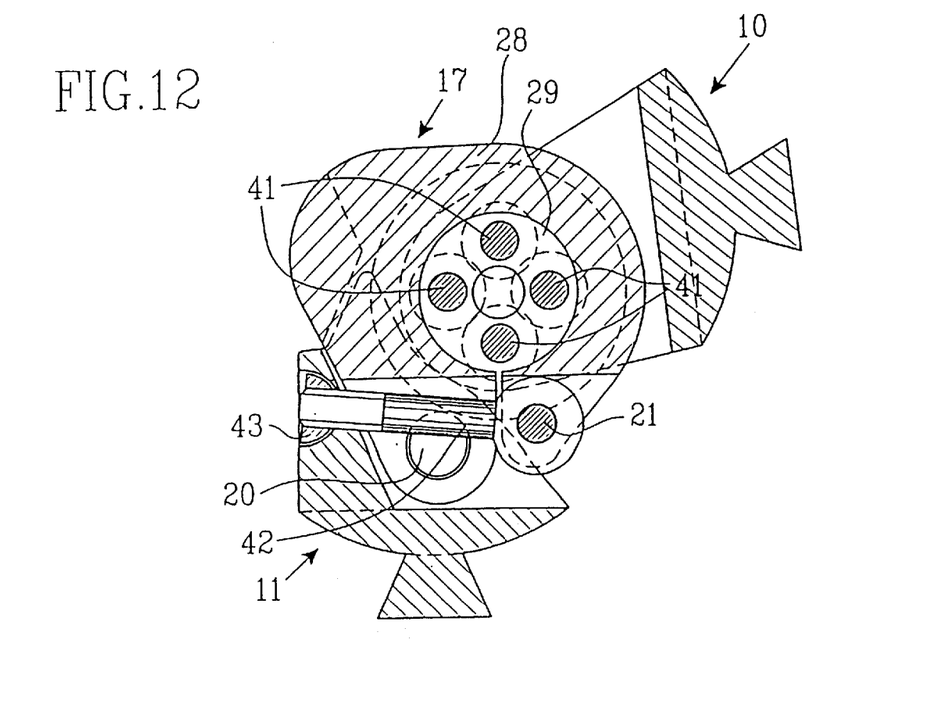
FIG. 12 is a corresponding section as FIG. 11 but showing the knee prosthesis in flexed position.
Figure 13:
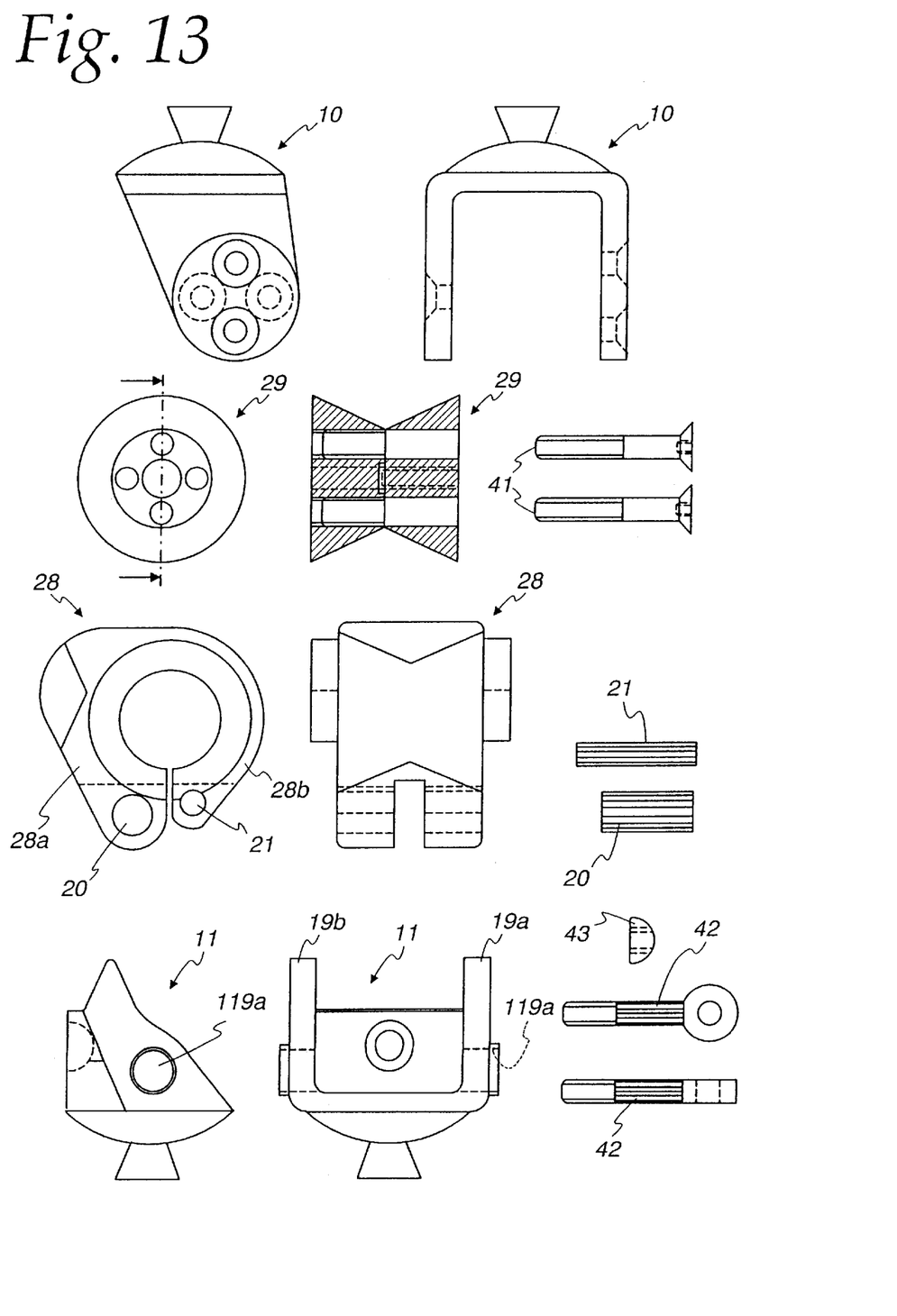
FIG. 13 is an exploded view of the knee prosthesis according to FIG. 11 and 12.

The embodiment according to FIGS. 11–13 are similar to the ones shown in FIGS. 6–7 by the fact that it also comprises a friction lock in the form of a substantially C-shaped resilient member 39 arranged to clamp about an axle for locking the knee joint. This axle in this case comprises a drum having the shape of two truncated cones interconnected at their narrow end surfaces. The drum 29 thus has two conical surfaces that taper towards the mid portion of the drum. The drum 29 is by means of mounting bolts 41 attached to the upper prosthesis member 10. By the conical design of the drum/pivot axle 29 axial as well as well as radial forces can effectively be taken up effectively, at which a laterally very stable knee joint is provided.

The first axle 20 extends through one shank 28a of the C-shaped member 28 acting as a bearing housing and brake clip and the second 28b. The brake-activating axle 21 is connected to the lower prosthesis member by means of the link 42 and the fastening member 43. The link 42 corresponds to the link 30 in FIG. 7.

When a force F is loading the knee joint behind the front axle 20 (FIG. 11) the C-shaped member 28 acting as a bearing and brake clip is forced to rotate downwards about the axle 20 in the direction of the arrow. The shank 28b will then pull the axle 20, which by its anchorage in the member 28 forces the same, while having the brake-activating axle 21 as a holder-on, to clamp about the drum 29 and by that lock the knee joint.

In all above described embodiments the relative placement of the two axles 20 and 21 is important for achieving the desired locking effect. Thus the first bearing axle 20 and the second brake-activating axle 21 should thus be located in such a position with respect to each other that the line of action 26 from a loading of the knee prosthesis in connection with toe off during the walking cycle will pass through the first axle 20 or in front thereof, so that the second axle 21 is unloaded and the locking device 17 inactivated. By this the knee prosthesis will only lock at heel strike and at mid stance while supporting oneself with the whole foot on the ground, while rotation is admitted when the knee joint is still loaded at toe off.

All described embodiments have a freewheel effect in such a way that the knee joint can always rotate from flexed to extended position also under load. By this for example walking in stairs will be possible. The knee-joint will however lock immediately again if it is rotated in the opposite direction, i e from extended to flexed position, under such load that the locking device is activated.

The invention is of course not limited to the embodiments shown in the drawings but can be modified within the scope of the following claims. It applies for example for all embodiments that the coupling means to the prosthesis sleeve and to the lower leg can be of another type than described herein.

What is claimed is:

1. A knee prosthesis comprising two pivotally interconnected members carrying a locking device and a first and a second axle, said first axle forming a bearing axle for the locking device and the second axle forming an activation mechanism of the locking device, wherein the interconnected members pivot about the first axle and said locking device is arranged to permit said members to pivot in an unloaded position but prevent pivoting from extended to bent position when loaded, wherein the second axle is located at a distance behind the first axle and is arranged to act upon the locking device in such a way that when the line of action from a load on the knee prosthesis passes through the second axle or between the first and the second axle, said second axle will act upon the locking device to activate it, while when said line of action passes through the first axle or in front of it the second axle will be unloaded and the locking device inactivated at which the locking device comprises a friction lock in the form of a brake drum which by means of the first axle is pivotally connected to one of said knee prosthesis members and which cooperates with the second axle in such a way that when the second axle is loaded the locking device will frictionally lock to the second knee prosthesis member, at which both knee prosthesis members will lock to each other, while when the second axle is unloaded they can be rotated with respect to each other, wherein the brake drum, which by means of the first axle is pivotally connected to one of said knee prosthesis members and which cooperates with the second axle in such a way that when the second axle is loaded, will expand and frictionally lock within the second knee prosthesis member designed as a bearing house, at which the two knee prosthesis members will lock to each other, while when the second axle is unloaded they can rotate with respect to each other, and wherein the brake drum is in the form of an open ring one end surface of which cooperates with the second axle.

2. A knee prosthesis comprising two pivotally interconnected members carrying a locking device and a first end a second axle, said first axle forming a bearing axle for the locking device and the second axle forming an activation mechanism of the locking device, wherein the interconnected members pivot about the locking device and the first and second axles thereof and said locking device is arranged to permit said members to pivot in an unloaded position but prevent pivoting from extended to bent position when loaded, wherein the second axle is located at a distance behind the first axle and is arranged to act upon the locking device in such a way that when the line of action from a load on the knee prosthesis passes through the second axle or between the first and the second axle, said second axle will act upon the locking device to activate it, while when said line of action passes through the first axle or in front of it the second axle will be unloaded and the locking device inactivated at which the locking device comprises a friction lock in the form of a brake drum or a brake clamp, which by means of the first axle is pivotally connected to one of said knee prosthesis members and which cooperates with the second axle in such a way that when the second axle is loaded the locking device will frictionally lock to the second knee prosthesis member, at which both knee prosthesis members will lock to each other, while when the second axle is unloaded they can be rotated with respect to each other, wherein the locking device comprises a brake drum, which by means of the first axle is pivotally connected to one of the knee prosthesis members and which cooperates with the second axle in such a way that when the second axle is loaded the brake drum will expand and frictionally lock within the second knee prosthesis member designed as a bearing housing, at which the two knee prosthesis members will lock to each other, while when the second axle is unloaded they can rotate with respect to each other and wherein the second axle cooperates with a lever arm which activated the brake drum against the action of a resilient element arranged between the brake drum and the lever arm on the opposite side thereof with respect to the second axle.

3. The knee prosthesis according to claim 2, wherein the resilient element is adjustable for adapting to the body weight of the prosthesis wearer.

4. A knee prosthesis comprising two pivotally interconnected members carrying a locking device and a first end a second axle, said first axle forming a bearing axle for the locking device and the second axle forming an activation mechanism of the locking device, wherein the interconnected members pivot about the locking device and the first and second axles thereof and said locking device is arranged to permit said members to pivot in an unloaded position but prevent pivoting from extended to bent position when loaded, wherein the second axle is located at a distance behind the first axle and is arranged to act upon the locking device in such a way that when the line of action from a load on the knee prosthesis passes through the second axle or between the first and the second axle, said second axle will act upon the locking device to activate it, while when said line of action passes through the first axle or in front of it the second axle will be unloaded and the locking device inactivated at which the locking device comprises a friction lock in the form of a brake drum or a brake clamp, which by means of the first axle is pivotally connected to one of said knee prosthesis members and which cooperates with the second axle in such a way that when the second axle is loaded the locking device will frictionally lock to the second knee prosthesis member, at which both knee prosthesis members will lock to each other, while when the second axle is unloaded they can be rotated with respect to each other, wherein the locking device comprises a brake drum, which by means of the first axle is pivotally connected to one of the knee prosthesis members and which cooperates with the second axle in such a way that when the second axle is loaded the brake drum will expand and frictionally lock within the second knee prosthesis member designed as a bearing housing, at which the two knee prosthesis members will lock to each other, while when the second axle is unloaded they can rotate with respect to each other and wherein the brake drum has the shape of an open ring and that a lever arm extends between a first and second shanks forming the opening of the open ring and to activation of the brake drum forces said shanks apart.

5. The knee prosthesis according to claim 4, wherein the first axle is mounted in one shank of the brake drum, while the second shank supports friction adjusting means.

* * * * *